US005734089A

United States Patent [19]
Thompson et al.

[11] Patent Number: 5,734,089
[45] Date of Patent: Mar. 31, 1998

[54] IN-SITU CONTINUOUS WATER MONITORING SYSTEM

[75] Inventors: Cyril V. Thompson, Knoxville; Marcus B. Wise, Kingston, both of Tenn.

[73] Assignee: Lockheed Martin Energy Systems, Inc., Oak Ridge, Tenn.

[21] Appl. No.: 710,226

[22] Filed: Sep. 12, 1996

[51] Int. Cl.$^6$ .................................................. G01N 1/22
[52] U.S. Cl. .................. 73/19.12; 73/64.56; 73/61.59; 95/263
[58] Field of Search ............................ 73/19.1, 19.12, 73/31.07, 61.59, 64.56, 863.21; 95/254, 263; 96/202

[56] References Cited

U.S. PATENT DOCUMENTS

| | | | |
|---|---|---|---|
| 3,800,595 | 4/1974 | Vincent | 73/19.1 |
| 3,942,792 | 3/1976 | Topol | 73/19.1 |
| 4,180,980 | 1/1980 | Marks et al. | 95/263 X |
| 4,613,347 | 9/1986 | Ranchet et al. | 96/202 X |
| 5,218,856 | 6/1993 | Doyle | 73/19.1 |
| 5,235,843 | 8/1993 | Langhorst | 73/19.02 |
| 5,272,337 | 12/1993 | Thompson et al. | 250/288 |
| 5,499,531 | 3/1996 | Hendrson | 73/64.45 |

OTHER PUBLICATIONS

M. Biziuk and J. Namiesnik, "New type of device for isolation of volatile organic compounds from aqueous samples based on generation of water–gas mixture," *Analusis*, 1989, v. 17, n 10, pp. 587–591.

Gerhard Matz and Peter Kesners, "Spray and Trap Method for Water Analysis by Thermal Desorption Gas Chromatography/Mass Spectrometry in Field Applications," *Anal. Chem.*, 1993, 65, 2366–2371.

Gokhan Baykut and Ansette Voigt, "Spray Extraction of Volatile Organic Compounds from Aqueous Systems into the Gas Phase for Gas Chromatography/Mass Spectrometry," *Anal. Chem.*, 1992, 64, 677–681.

Scott J. Bauer and R. Graham Cooks, "MIMS for trace–level determination of organic analytes in on–line process monitoring and environmental analysis," *American Laboratory*, Oct. 1993, 36–51.

*Primary Examiner*—Michael Brock
*Attorney, Agent, or Firm*—Ivan L. Ericson

[57] ABSTRACT

An in-situ continuous liquid monitoring system for continuously analyzing volatile components contained in a water source comprises: a carrier gas supply, an extraction container and a mass spectrometer. The carrier gas supply continuously supplies the carrier gas to the extraction container and is mixed with a water sample that is continuously drawn into the extraction container by the flow of carrier gas into the liquid directing device. The carrier gas continuously extracts the volatile components out of the water sample. The water sample is returned to the water source after the volatile components are extracted from it. The extracted volatile components and the carrier gas are delivered continuously to the mass spectrometer and the volatile components are continuously analyzed by the mass spectrometer.

15 Claims, 2 Drawing Sheets

IN-SITU CONTINUOUS WATER MONITORING SYSTEM

This invention was made with Government support under contract DE-AC05-84OR21400 awarded by the U.S. Department of Energy to Lockheed Martin Energy Systems, Inc. and the Government has certain rights in this Invention.

FIELD OF THE INVENTION

The present invention relates to a water monitoring system, more particularly, to an in-situ continuous water monitoring system.

BACKGROUND OF THE INVENTION

Previous water analyses for volatile organic compounds have been performed by purge-and-trap gas chromatography/mass spectrometry or by direct sampling ion trap mass spectrometry by taking a representative aliquot of the water, typically 40 ml in a glass vial sealed with a Teflon-lined septum cap, and analyzing it by the requisite means. Analysis by purge-and-trap gas chromatography/mass spectrometry took up to one hour per sample, while analysis by direct sampling ion trap mass spectrometry took around three minutes. Although the direct sampling ion trap mass spectrometry method was considerably faster, it still required that a sample be acquired from sites such as wells, surface water bodies, seeps, etc. Acquiring samples from wells generally involves purging three well volumes prior to taking the first sample for analysis. Both methods also require extensive paper work to maintain chain-of-custody record.

OBJECTS OF THE INVENTION

Accordingly, it is an object of the present invention to provide an in-situ continuous water monitoring system. Further and other objects of the present invention will become apparent from the description contained herein.

SUMMARY OF THE INVENTION

In accordance with one aspect of the present invention, a new and improved in-situ continuous liquid monitoring system for continuously analyzing volatile components of a liquid in a liquid source having a surface and a sampling depth comprising: a carrier gas supply means for continuously supplying a carrier gas, a carrier gas directing means, a sample gas analyzing means for continuously extracting the volatile components contained in the liquid, an extraction container having an outside surface and a liquid source surface level on the outside surface, a liquid directing means having a carrier gas inlet port, a liquid inlet port and a liquid outlet port, a liquid level indicating means positioned on the outside surface of the extraction container at the liquid source surface level for indicating the surface of the liquid source on the outside surface of the extraction container and a liquid inlet port depth positioning means for positioning the liquid inlet port of the liquid directing means at the sampling depth. The extraction container has a carrier gas inlet port, a sample gas outlet port, a liquid outlet port and a support means for said liquid directing means. The sample gas analyzing means has a sample gas inlet port. The extraction container has a first end and a second end. The extraction container has the carrier gas inlet port and the sample gas outlet at the first end and the liquid outlet port at the second end. The liquid outlet port at the second end of the extraction container is positioned parallel to and below the surface of the liquid source. The liquid directing means extends into the extraction container through the liquid outlet port of the extraction container and supported by the support means of the extraction container. The liquid outlet port of the liquid directing means is positioned within the extraction container and the liquid inlet port of the liquid directing means is positioned outside the extraction container. The carrier gas supply is in communication with the carrier gas inlet port of the extraction container. The carrier gas directing means has a carrier gas inlet port and a carrier gas outlet port. The carrier gas inlet port of the carrier gas directing means is in communication with the carrier gas inlet port of the extraction container. The said sample gas outlet port of the extraction container is in communication with the sample gas inlet port of the gas analyzing means the liquid directing means is in communication with and supported by the support means of the extraction container.

In accordance with another aspect of the present invention a new and improved method for an in-situ continuous liquid monitoring system for continuously analyzing volatile components of a liquid in a liquid source comprises the following steps:

Step 1. An in-situ continuous liquid monitoring system is provided for continuously analyzing volatile components of a liquid in a liquid source having a surface and a sampling depth comprising: a carrier gas supply means for continuously supplying a carrier gas, a carrier gas directing means, a sample gas analyzing means for continuously extracting the volatile components contained in the liquid, an extraction container having an outside surface and a liquid source surface level on the outside surface, a liquid directing means having a carrier gas inlet port, a liquid inlet port and a liquid outlet port, a liquid level indicating means positioned on the outside surface of the extraction container at the liquid source surface level for indicating the surface of the liquid source on the outside surface of the extraction container and a liquid inlet port depth positioning means for positioning the liquid inlet port of the liquid directing means at the sampling depth. The extraction container has a carrier gas inlet port, a sample gas outlet port, a liquid outlet port and a support means for said liquid directing means. The sample gas analyzing means has a sample gas inlet port. The extraction container has a first end and a second end. The extraction container has the carrier gas inlet port and the sample gas outlet at the first end and the liquid outlet port at the second end. The liquid outlet port at the second end of the extraction container is positioned parallel to and below the surface of the liquid source. The liquid directing means extends into the extraction container through the liquid outlet port of the extraction container and is supported by the support means of the extraction container. The liquid outlet port of the liquid directing means is positioned within the extraction container and the liquid inlet port of the liquid directing means is positioned outside the extraction container. The carrier gas supply is in communication with the carrier gas inlet port of the extraction container. The carrier gas directing means has a carrier gas inlet port and a carrier gas outlet port. The carrier gas inlet port of the carrier gas directing means is in communication with the carrier gas inlet port of the extraction container. The said sample gas outlet port of the extraction container is in communication with the sample gas inlet port of the gas analyzing means. The liquid directing means is in communication with and supported by the support means of the extraction container, Step 2. The extraction container is positioned in the liquid source to be tested at a position where the surface of the liquid source is located at the liquid source surface level of the extraction means.

Step 3. The liquid inlet port of the liquid directing means is positioned within said liquid source at the sampling depth of the liquid source by the liquid inlet port depth positioning means.

Step 4. The liquid is continuously drawn from the liquid source into the liquid inlet port of the liquid directing means and the liquid is flowed through the liquid directing means by the carrier gas flowing into the liquid directing means through the carrier gas inlet port of the liquid directing means. The carrier gas contacts the liquid flowing within the liquid directing means for a period of time sufficient to extract the volatile components within the flowing liquid forming a sample gas. The sample gas containing the extracted volatile components of the liquid and the carrier gas exits the liquid directing means into the extraction container and exits through the sample gas outlet port of the extraction container into the sample gas inlet port of the sample gas analyzing means.

Step 5. The volatile components in the sample gas are continuously analyzed with the analyzing means.

For a better understanding of the present invention, together with other and further objects, advantages and capabilities thereof, reference is made to the following disclosure and appended claims in connection with the above described drawings.

DETAILED DESCRIPTION OF THE PREFERRED EMBODIMENTS

The present invention eliminates the requirement for actually acquiring a separate sample, as it operates on the water sample in-situ, wherever that might be. Analyses of volatile organic compounds in water can be performed on any water sample that the in-situ water monitor of the present invention can be deployed in, including deep water wells. Use of this device eliminates the sample acquisition, paperwork for chain-of-custody records, and disposal of the processed sample which are required for the previously mentioned methods. The sensitivity of the system of the present invention is comparable to that achievable with the soil/water purge system previously patented by the inventors in U.S. Pat. No. 5,272,337. It has been deployed twice in field tests with great success, with a monitoring rate for wells of about 4 per hour. It can also be deployed with devices such as cone penetrometers (via hydro-punch) or Geoprobes. An added benefit is that analytical results are available immediately in the field at the site of characterization or remediation, where they can be used to direct pertinent field operations such as well placement or groundwater treatment.

Figure 1:
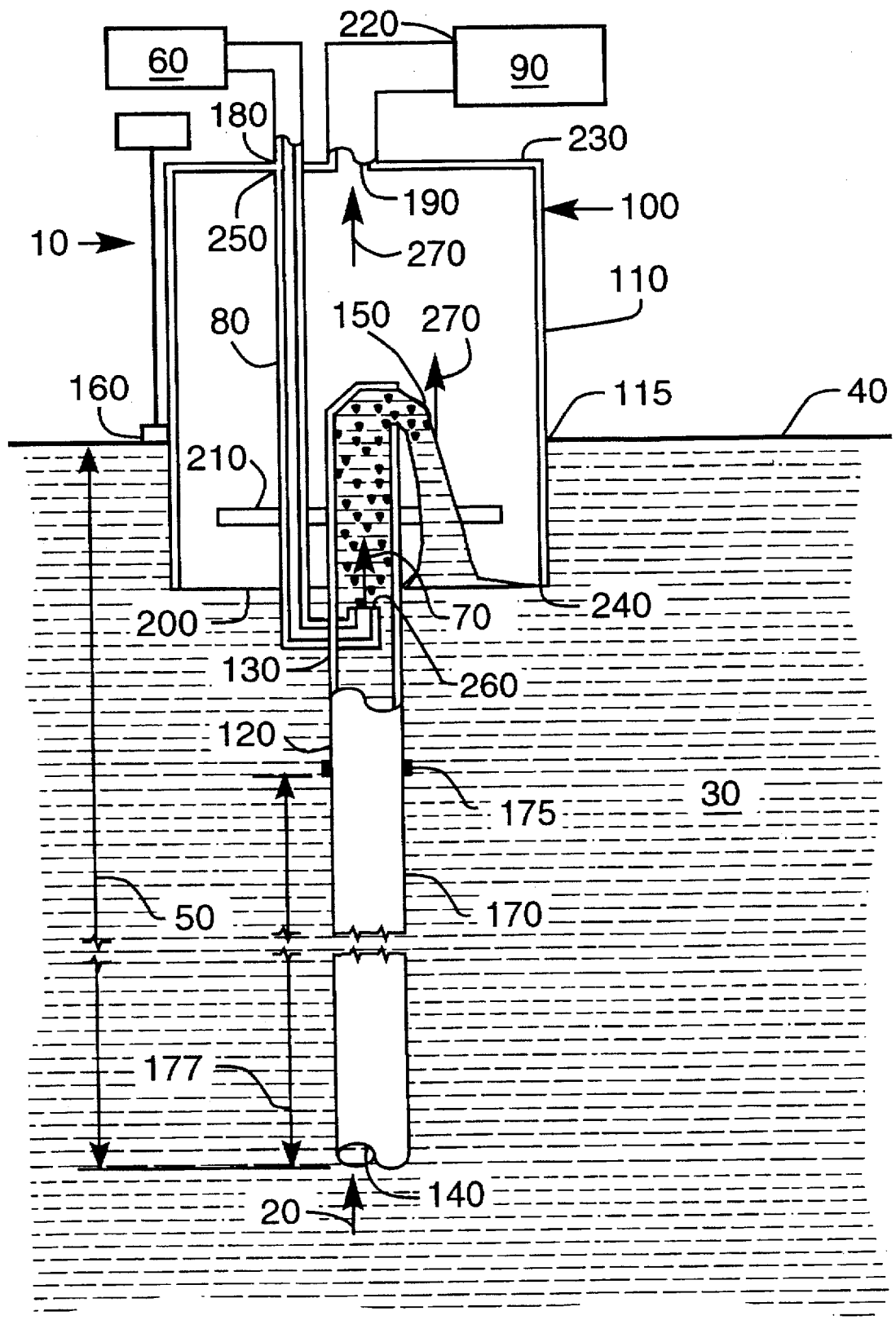
FIG. 1 is a cross-sectional view of an in-situ continuous liquid monitoring system in accordance with the present invention.

Shown in FIG. 1 is in-situ continuous liquid monitoring system 10 for continuously analyzing volatile components of liquid 20 in liquid source 30 having surface 40 and sampling depth 50. In-situ continuous liquid monitoring system 10 comprises: carrier gas supply means 60, such as a pressurized gas cylinder of helium having a pressure regulator and a flow meter attached thereto, for continuously supplying carrier gas 70, carrier gas directing means 80, such as a tube, sample gas analyzing means 90, such as a mass spectrometer as described in U.S. Pat. No. 5,272,337 to Thompson et al incorporated herein by reference thereto, for continuously extracting the volatile components contained in liquid 20, extraction container 100 having outside surface 110 and liquid source surface level 115 on outside surface 110 of extraction container 100, liquid directing means 120, such as a tube, having carrier gas inlet port 130, liquid inlet port 140 and liquid outlet port 150, liquid level indicating means 160 positioned on outside surface 110 of extraction container 100 at liquid source surface level 115 for indicating surface 40 of liquid source 30 on outside surface 110 of extraction container 100 and liquid inlet port depth positioning means 170, such as a stainless steel tube, having liquid inlet port 140 and attaching means 175 for attaching liquid inlet port depth positioning means 170 to liquid directing means 120. Liquid inlet port depth positioning means 170 has a length 177 sufficient to position liquid inlet port 140 at sampling depth 50. Depending upon the desired sampling depth 50 length 177 of liquid inlet port depth positioning means 170 will vary to position liquid inlet port 140 of liquid directing means 120 at sampling depth 50. Extraction container 100, liquid directing means 120, liquid inlet port depth positioning means 170 and carrier gas directing means 80 can be made from stainless steel or any material which will not be harmed by liquid 20 or react with the volatile components of liquid 20. Extraction container 100 has carrier gas inlet port 180, sample gas outlet port 190, liquid outlet port 200 and support means 210 for supporting liquid directing means 120. Sample gas analyzing means 90 has sample gas inlet port 220. Extraction container 100 has first end 230 and second end 240. Extraction container 100 has carrier gas inlet port 180 and sample gas outlet port 190 at first end 230 and liquid outlet port 200 at second end 240. Liquid outlet port 200 at second end 240 of extraction container 100 is positioned parallel to and below surface 40 of liquid source 30. Liquid directing means 120 extends into extraction container 100 through liquid outlet port 200 of extraction container 100 and is supported by support means 210 of extraction container 100. Liquid outlet port 150 of liquid directing means 120 is positioned within extraction container 100 and liquid inlet port 140 of liquid directing means 120 is positioned outside extraction container 100. Carrier gas supply 60 is in communication with carrier gas inlet port 180 of extraction container 100. Carrier gas directing means 80 has carrier gas inlet port 250 and carrier gas outlet port 260. Carrier gas inlet port 250 of carrier gas directing means 80 is in communication with carrier gas inlet port 180 of extraction container 100. Sample gas outlet port 190 of extraction container 100 is in communication with sample gas inlet port 220 of gas analyzing means 90. Liquid directing means 120 is in communication with and supported by support means 210 of extraction container 100.

The method for continuously analyzing volatile components of liquid 20 in liquid source 30 comprises the following steps:

Step 1. An in-situ continuous liquid monitoring system 10 is provided for continuously analyzing volatile components of liquid 20 in liquid source 30 having surface 40 and sampling depth 50. In-situ continuous liquid monitoring system 10 comprises: carrier gas supply means 60, such as a pressurized gas cylinder of helium having a pressure regulator and a flow meter attached thereto, for continuously supplying carrier gas 70, carrier gas directing means 80, such as a tube, sample gas analyzing means 90 such as a mass spectrometer as described in U.S. Pat. No. 5,272,337 to Thompson et al incorporated herein by reference thereto, for continuously extracting the volatile components contained in liquid 20, extraction container 100 having outside surface 110 and liquid source surface level 115 on outside surface 110 of extraction container 100, liquid directing means 120, such as a tube, having carrier gas inlet port 130, liquid inlet port 140 and liquid outlet port 150, liquid level indicating means 160 positioned on outside surface 110 of extraction container 100 at liquid source surface level 115 for indicating surface 40 of liquid source 30 on outside surface 110 of extraction container 100 and liquid inlet port depth positioning means 170, such as a stainless steel tube, having liquid inlet port 140 and attaching means 175 for attaching liquid inlet port depth positioning means 170 to liquid directing means 120. Liquid inlet port depth positioning means 170 has a length 177 sufficient to position liquid inlet port 140 at sampling depth 50. Depending upon the desired sampling depth 50 length 177 of liquid inlet port depth positioning means 170 will vary to position liquid inlet port 140 of liquid directing means 120 at sampling depth 50. Extraction container 100, liquid directing means 120, liquid inlet port depth positioning means 170 and carrier gas directing means 80 can be made from stainless steel or any material which will not be harmed by the liquid to be sampled or react with the volatile components. Extraction container 100 has carrier gas inlet port 180, sample gas outlet port 190, liquid outlet port 200 and support means 210 for supporting liquid directing means 120. Sample gas analyzing means 90 has sample gas inlet port 220. Extraction container 100 has first end 230 and second end 240. Extraction container 100 has carrier gas inlet port 180 and sample gas outlet port 190 at first end 230 and liquid outlet port 200 at second end 240. Liquid outlet port 200 at second end 240 of extraction container 100 is positioned parallel to and below surface 40 of liquid source 30. Liquid directing means 120 extends into extraction container 100 through liquid outlet port 200 of extraction container 100 and supported by support means 210 of extraction container 100. Liquid outlet port 150 of liquid directing means 120 is positioned within extraction container 100 and liquid inlet port 140 of liquid directing means 120 is positioned outside extraction container 100. Carrier gas supply 60 is in communication with carrier gas inlet port 180 of extraction container 100. Carrier gas directing means 80 has carrier gas inlet port 250 and carrier gas outlet port 260. Carrier gas inlet port 250 of carrier gas directing means 80 is in communication with carrier gas inlet port 180 of extraction container 100. Sample gas outlet port 190 of extraction container 100 is in communication with sample gas inlet port 220 of gas analyzing means 90. Liquid directing means 120 is in communication with and supported by support means 210 of extraction container 100.

Step 2. Extraction container 100 is positioned in liquid source 30 to be tested at a position where surface 40 of liquid source 30 is located at liquid source surface level 115 of extraction means 100 (When surface 40 of liquid source 30 at liquid source surface level 115 cannot be ascertained visually, liquid level detection means 160, such as a conductivity indicator, is fastened to side 110 of extraction container 100 and is used to position extraction container 100 at liquid source surface level 115).

Step 3. Liquid inlet port 140 of liquid directing means 120 is positioned within liquid source 30 at sampling depth 50 of liquid source 30 by liquid inlet port depth positioning means 170.

Step 4. Liquid 20 is continuously drawn from liquid source 30 into liquid inlet port 140 and flowed through liquid directing means 120 and out of liquid outlet port 150 of liquid directing means 120 by carrier gas 70 flowing into liquid directing means 120 through carrier gas outlet port 260 positioned within liquid directing means creating a pumping action which draws liquid 20 into liquid inlet port 140, thus refreshing liquid 20 from source liquid 30 inside liquid directing means 120 continually. Carrier gas 70 contacts liquid 20 flowing within liquid directing means 120 for a period of time sufficient to extract the volatile components within flowing liquid 20 forming a sample gas 270. Sample gas 270 containing the extracted volatile components of liquid 20 and carrier gas 70 exits liquid outlet port 150 of liquid directing means 120 into extraction container 100 and exits through sample gas outlet port 190 of extraction container 100 into sample gas inlet port 220 of sample gas analyzing means 90.

Step 5. The volatile components in sample gas 270 are continuously analyzed with analyzing means 90.

Figure 2:
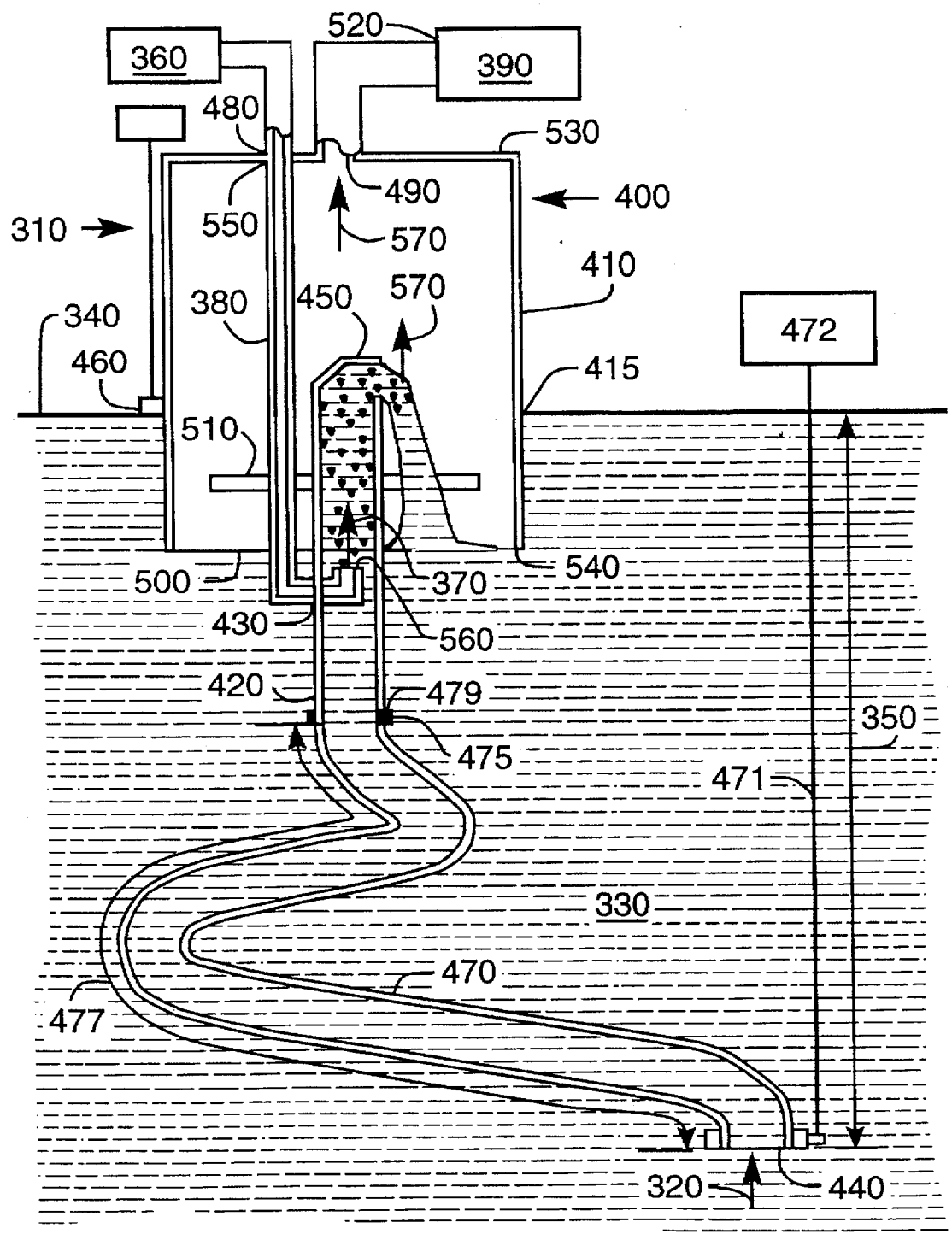
FIG. 2 is a cross-sectional view of another aspect of an in-situ continuous liquid monitoring system in accordance with the present invention.

Shown in FIG. 2 is in-situ continuous liquid monitoring system 310 for continuously analyzing volatile components of liquid 320 in liquid source 330 having surface 340 and sampling depth 350. In-situ continuous liquid monitoring system 310 comprises: carrier gas supply means 360, such as a pressurized gas cylinder of helium having a pressure regulator and a valved flow meter attached thereto, for continuously supplying carrier gas 370, carrier gas directing means 380, such as a tube, sample gas analyzing means 390 such as a mass spectrometer as described in U.S. Pat. No. 5,272,337 to Thompson et al incorporated herein by reference thereto, for continuously extracting the volatile components contained in liquid 320, extraction container 400 having outside surface 410 and liquid source surface level 415 on outside surface 410 of extraction container 400, liquid directing means 420, such as a tube, having carrier gas inlet port 430, liquid inlet port 440 and liquid outlet port 450, liquid level indicating means 460 positioned on outside surface 410 of extraction container 400 at liquid source surface level 415 for indicating surface 340 of liquid source 330 on outside surface 410 of extraction container 400 and liquid inlet port depth positioning means 470, such as a flexible stainless steel tube, having liquid inlet port 440 and attaching means 475 for attaching liquid inlet port depth positioning means 470 to liquid directing means 420. Liquid inlet port depth positioning means 470 has a length 477 sufficient to position liquid inlet port 440 at sampling depth 350. Depending upon the desired sampling depth 350, length 477 of liquid inlet port depth positioning means 470 will vary to position liquid inlet port 440 of liquid directing means 420 at sampling depth 350. Extraction container 400, liquid directing means 420, liquid inlet port depth positioning means 470 and carrier gas directing means 380 can be made from stainless steel or any material which will not be harmed by liquid 320 or react with the volatile components of liquid 320. Extraction container 400 has carrier gas inlet port 480, sample gas outlet port 490, liquid outlet port 500 and support means 510 for supporting liquid directing means 420. Sample gas analyzing means 390 has sample gas inlet port 520. Extraction container 400 has first end 530 and second end 540. Extraction container 400 has carrier gas inlet port 480 and sample gas outlet port 490 at first end 530 and liquid outlet port 500 at second end 540. Liquid outlet port 500 at second end 540 of extraction container 400 is positioned parallel to and below surface 340 of liquid source 330. Liquid directing means 420 extends into extraction container 400 through liquid outlet port 500 of extraction container 400 and is supported by support means 510 of extraction container 400. Liquid outlet port 450 of liquid directing means 420 is positioned within extraction container 400 and liquid inlet port 440 of liquid directing means 420 is positioned outside extraction container 400. Carrier gas supply 360 is in communication with carrier gas inlet port 480 of extraction container 400. Carrier gas directing means 380 has carrier gas inlet port 550 and carrier gas outlet port 560. Carrier gas inlet port 550 of carrier gas directing means 380 is in communication with carrier gas inlet port 480 of extraction container 400. Sample gas outlet port 490 of extraction container 400 is in communication with sample gas inlet port 520 of gas analyzing means 390. Liquid directing means 420 is in communication with and supported by support means 510 of extraction container 400.

The method for continuously analyzing volatile components of liquid 320 in liquid source 330 comprises the following steps:

Step 1. An in-situ continuous liquid monitoring system 310 is provided for continuously analyzing volatile components of liquid 320 in liquid source 330 having surface 340 and sampling depth 350. In-situ continuous liquid monitoring system 310 comprises: carrier gas supply means 360, such as a pressurized gas cylinder of helium having a pressure regulator and a flow meter attached thereto, for continuously supplying carrier gas 370, carrier gas directing means 380, such as a tube, sample gas analyzing means 390, such as a mass spectrometer as described in U.S. Pat. No. 5,272,337 to Thompson et al incorporated herein by reference thereto, for continuously extracting the volatile components contained in liquid 320, extraction container 100 having outside surface 410 and liquid source surface level 415 on outside surface 410 of extraction container 400, liquid directing means 420, such as a tube, having carrier gas inlet port 430, first end 479 and liquid outlet port 450, liquid level indicating means 460 positioned on outside surface 410 of extraction container 400 at liquid source surface level 415 for indicting surface 340 of liquid source 330 on outside surface 410 of extraction container 400 and liquid inlet port depth positioning means 470, such as flexible tubing, having liquid inlet port 440 and attaching means 475 for attaching liquid inlet port depth positioning means 470 to first end 479 of liquid directing means 420. Liquid inlet port depth positioning means 470 has a length 477 sufficient to position liquid inlet port 440 at desired sampling depth 350. Length 477 of liquid inlet port depth positioning means 470 is constant, but the position of liquid inlet port 440 of liquid directing means 420 will vary depending upon the desired sampling depth 350. Liquid inlet port depth changing means 472, such as a winch, having cable 471 attached to liquid inlet port 440 changes sampling depth by raising or lower cable 471. Extraction container 400, liquid directing means 420, liquid inlet port depth positioning means 470 and carrier gas directing means 380 can be made from any material which will not be harmed by the liquid to be sampled or react with the volatile components. Extraction container 400 has carrier gas inlet port 480, sample gas outlet port 490, liquid outlet port 500 and support means 510 for supporting liquid directing means 420. Sample gas analyzing means 390 has sample gas inlet port 520. Extraction container 400 has first end 530 and second end 540. Extraction container 400 has carrier gas inlet port 480 and sample gas outlet port 490 at first end 530 and liquid outlet port 500 at second end 540. Liquid outlet port 500 at second end 540 of extraction container 400 is positioned parallel to and below surface 340 of liquid source 330. Liquid directing means 420 extends into extraction container 400 through liquid outlet port 500 of extraction container 400 and is supported by support means 510 of extraction container 400.

Liquid outlet port 450 of liquid directing means 420 is positioned within extraction container 400 and liquid inlet port 440 of liquid directing means 420 is positioned outside extraction container 400. Carrier gas supply 360 is in communication with carrier gas inlet port 480 of extraction container 400. Carrier gas directing means 380 has carrier gas inlet port 550 and carrier gas outlet port 560. Carrier gas inlet port 550 of carrier gas directing means 380 is in communication with carrier gas inlet port 480 of extraction container 400. Sample gas outlet port 490 of extraction container 400 is in communication with sample gas inlet port 520 of gas analyzing means 390. Liquid directing means 420 is in communication with and supported by support means 510 of extraction container 400.

Step 2. Extraction container 400 is positioned in liquid source 330 to be tested at a position where surface 340 of liquid source 330 is located at liquid source surface level 415 of extraction means 400 (When surface 340 of liquid source 330 at liquid source surface level 415 cannot be ascertained visually, liquid level detection means 460, such as a conductivity indicator, is fastened to side 410 of extraction container 400 and is used to position extraction container 400 at liquid source surface level 415).

Step 3. Liquid inlet port 440 of liquid directing means 420 is positioned within liquid source 330 at sampling depth 350 of liquid source 330 by liquid inlet port depth positioning means 470.

Step 4. Liquid 320 is continuously drawn from liquid source 330 into liquid inlet port 440 and flowed through liquid directing means 420 and out of liquid outlet port 450 of liquid directing means 420 by carrier gas 370 flowing into liquid directing means 420 through carrier gas outlet port 560 positioned within liquid directing means creating a pumping action which draws liquid 320 into liquid inlet port 440, thus refreshing liquid 320 from source liquid 330 inside liquid directing means 320 continually. Carrier gas 370 contacts liquid 320 flowing within liquid directing means 420 for a period of time sufficient to extract the volatile components within flowing liquid 320 forming a sample gas 570. Sample gas 570 containing the extracted volatile components of liquid 320 and carrier gas 370 exits liquid outlet port 450 of liquid directing means 420 into extraction container 400 and exits through sample gas outlet port 490 of extraction container 400 into sample gas inlet port 520 of sample gas analyzing means 390.

Step 5. The volatile components in sample gas 570 are continuously analyzed with analyzing means 390.

A particular advantage of this invention is the ability to sample a liquid from different depths of a liquid source to be analyzed. This is accomplished by extending the length of the liquid directing means by connecting the liquid directing means extension, such as an additional length of tubing to the liquid directing means to relocate the liquid inlet port to the desired sampling depth. Since the pumping action created by the flow of the carrier gas into the liquid directing means is determined by the pressure differential created by the depth below the surface of the liquid source of the carrier gas outlet port and the surface of the liquid source, any amount of tubing can be added to the liquid directing means to accomplish the desired depth of the liquid inlet port. Obviously, the more tubing added, the slower the response time of the analysis of the volatile components in the liquid source due to the lag time required for the liquid to pass completely through the liquid inlet port depth positioning means extension and the liquid directing means.

The extraction container, liquid directing means and the carrier gas directing means of the present invention requires no moving pads, no electrical power, and can be deployed in very small spaces.

Varying versions of this invention can be designed for and permanently deployed in wells at very little cost, permitting in-situ sampling of the wells and eliminating costly bailing/ pumping of the well for sample acquisition. Versions could be developed which would be adapted for use with ground penetrating probes as mentioned above.

This system could be used for field characterization of volatile organic compounds in water at suspected hazardous waste sites, for remediation monitoring of confirmed sites, for spot sampling of surface water to track chemical plumes, and for quick characterization of volatile organic compounds in any surface water. The demand for this system should greatly exceed that of the previous soil/water purge system due to its great flexibility of deployment. Both government and industry have considerable need for the capability provided by this invention.

The present invention provides for the immediate quantitation of volatile organic compounds in water. It also provides for the real-time monitoring of such compounds in water samples or process streams. Variations in the concentrations of these compounds can be detected and plotted in real-time. The present invention has been used successfully to monitor the volatiles levels in seep water as a water supply was being treated. The concentrations of a number of volatile organic compounds, such as toluene, benzene, methyl ethyl ketone, TCA, DCA, xylenes, ethylbenzene and C2-Benzenes, were continuously followed during the treatment process for destroying the compounds.

One advantage of the present invention is that no water samples need be transferred, treated and then disposed of, especially if the samples are classified as a hazardous waste, a significant benefit over other methods of water analysis.

Another aspect of the present invention provides a device which can conduct depth profiling of volatile organic compounds contained in a body of water. The head pressure, as well as a slight positive carrier gas flow, must be maintained in the extraction container to prevent water from being entrained in the umbilical cord and entering the analyzer. The umbilical cord at the bottom of the liquid directing means can be used to increase the contact between the helium carrier gas and the water being sampled by installing a flexible helium carrier gas directing means beside or within the liquid directing means and the flexible umbilical cord with the helium carrier gas outlet of the helium carrier gas directing means positioned towards the bottom of the umbilical cord but above the liquid inlet port of the liquid directing means. This should increase the response of the analyzer to the analytes, by increasing the concentration of analytes in the sample gas.

The umbilical to the extraction container consists of tubing for the carrier gas (TFE, 1/16" OD, 1/32"ID) and return tubing for the sample gas (TFE, 1/8"OD–1/16"ID or stainless steel, 1/16"od–0.040"id). The size of the carrier gas tubing is small to maintain a low profile umbilical. The size of the return tubing is small to lower the dead volume of the return tubing and to minimize the delay in response time from the point in time at which the water enters the sampling device to the point at which an analytical response is seen in the analyzer.

The present arrangement of this sampling device also permits the device to be independently monitored by spiking the carrier gas stream with an aliquot of an inert gas, such as Argon, to confirm proper operation of the analyzer and to determine the response time of the sampling device.

While there has been shown and described what is at present considered the preferred embodiments of the invention, it will be obvious to those skilled in the art that various changes and modifications may be made therein without departing from the scope of the invention as defined by the appended claims.

What is claimed is:

1. An in-situ continuous liquid monitoring system for continuously analyzing volatile components of a liquid in a liquid source having a surface and a sampling depth comprising: a carrier gas supply means for continuously supplying a carrier gas, a carrier gas directing means, a sample gas analyzing means for continuously analyzing the volatile components contained in said liquid, an extraction container having an outside surface and a liquid source surface level on said outside surface, a liquid directing means having a carrier gas inlet port, a liquid inlet port and a liquid outlet port, a liquid level indicating means positioned on said outside surface of said extraction container at said liquid source surface level for indicating said surface of said liquid source on said outside surface of said extraction container and a liquid inlet port depth positioning means for positioning said liquid inlet port of said liquid directing means at said sampling depth, said extraction container having a carrier gas inlet port, a sample gas outlet port, a liquid outlet port and a support means for said liquid directing means, said sample gas analyzing means having a sample gas inlet port, said extraction container having a first end and a second end, said extraction container having said carrier gas inlet port and said sample gas outlet at said first end and said liquid outlet port at said second end, said liquid outlet port at said second end of said extraction container being positioned parallel to and below said surface of said liquid source, said liquid directing means extending into said extraction container through said liquid outlet port of said extraction container and supported by said support means of said extraction container, said liquid outlet port of said liquid directing means being positioned within said extraction container and said liquid inlet port of said liquid directing means being positioned outside said extraction container, said carrier gas supply being in communication with said carrier gas inlet port of said extraction container, said carrier gas directing means having a carrier gas inlet port and a carrier gas outlet port, said carrier gas inlet port of said carrier gas directing means being in communication with said carrier gas inlet port of said extraction container, said sample gas outlet port of said extraction container being in communication with said sample gas inlet port of said gas analyzing means, said liquid directing means being connected to and supported by said support means of said extraction container, said liquid inlet port depth positioning means has an attaching means and a liquid inlet port, said liquid inlet port depth positioning means is a flexible length of tubing attached to said liquid directing means by said attaching means, said flexible length of flexible tubing has a first end and a second end, said flexible length of tubing has said liquid inlet port attached to said first end of said flexible length of tubing and said attaching means attached to said second end of said flexible length of tubing, said liquid inlet port depth positioning means has a liquid inlet port depth changing means attached thereto by a cable.

2. An in-situ continuous liquid monitoring system in accordance with claim 1 wherein said liquid is water.

3. An in-situ continuous liquid monitoring system in accordance with claim 1 wherein said carrier gas is helium.

4. An in-situ continuous liquid monitoring system in accordance with claim 1 wherein said carrier gas supply means is a pressurized gas cylinder of helium having a pressure regulator and a valved flow meter.

5. An in-situ continuous liquid monitoring system in accordance with claim 1 wherein said sample gas analyzing means is a mass spectrometer.

6. An in-situ continuous liquid monitoring system in accordance with claim 1 wherein said liquid directing means extension is a length of tubing attached to said liquid directing means.

7. An in-situ continuous liquid monitoring/system in accordance with claim 1 wherein said liquid directing means extension is a flexible length of tubing attached to said liquid directing means, said flexible length of tubing has said liquid inlet port attach to said first end of said flexible length of tubing and a liquid inlet port depth positioning means attached thereto.

8. An in-situ continuous liquid monitoring system in accordance with claim 1 wherein said liquid inlet port depth changing means is a winch with a cable attached at one end to said liquid inlet port and attached at the other end to said liquid inlet port depth changing means for lowering and raising said liquid inlet port in said liquid source.

9. A method for continuously analyzing volatile components of a liquid in a liquid source comprising the following steps;

Step 1. providing an in-situ continuous liquid monitoring system for continuously analyzing volatile components of a liquid in a liquid source having a surface and a sampling depth comprising: a carrier gas supply means for continuously supplying a carrier gas, a carrier gas directing means, a sample gas analyzing means for continuously analyzing the volatile components contained in said liquid, an extraction container having an outside surface, a liquid directing means having a carrier gas inlet port, a liquid inlet port and a liquid outlet port, a liquid level indicating means for indicating said surface of said liquid source on said outside surface of said extraction container and a liquid inlet port depth positioning means for positioning said liquid inlet port of said liquid directing means at said sampling depth, said extraction container having a carrier gas inlet port, a sample gas outlet port, a liquid outlet port and a support means for said liquid directing means, said sample gas analyzing means having a sample gas inlet port, said extraction container having a first end and a second end, said extraction container having said carrier gas inlet port and said sample gas outlet at said first end and said liquid outlet port at said second end, said liquid outlet port at said second end of said extraction container being positioned parallel to and below said surface of said liquid source, said liquid directing means extending into said extraction container through said liquid outlet port of said extraction container and supported by said support means of said extraction container, said liquid outlet port of said liquid directing means being positioned within said extraction container and said liquid inlet port of said liquid directing means being position outside said extraction container, said carrier gas supply being in communication with said carrier gas inlet port of said extraction container, said carrier gas directing means having a carrier gas inlet port and a carrier gas outlet port, said carrier gas inlet port of said carrier gas directing means being in communication with said carrier gas inlet port of said extraction container, said sample gas outlet port of said extraction container being in communication with said sample gas inlet port of said gas analyzing means, said liquid directing means being connected to and supported by said support means of said extraction container, said liquid inlet port depth positioning means has an attaching means and a liquid inlet port, said liquid inlet port depth positioning means is a flexible length of tubing attached to said liquid directing means by said attaching means, said flexible length of flexible tubing has a first end and a second end, said flexible length of tubing has said liquid inlet port attached to said first end of said flexible length of tubing and said attaching means attached to said second end of said flexible length of tubing, said liquid inlet port depth positioning means has a liquid inlet port depth changing means attached thereto by a cable;

Step 2. positioning said extraction container in said liquid source to be tested at a position where said surface of said liquid source is located at said liquid source surface level of said extraction means;

Step 3. positioning said liquid inlet port of said liquid directing means within said liquid source at said sampling depth of said liquid source by said liquid inlet port depth positioning means;

Step 4. continuously drawing said liquid from said liquid source into said liquid inlet port of said liquid directing means and flowing said liquid through said liquid directing means by said carrier gas flowing into said liquid directing means through said carrier gas inlet port of said liquid directing means, said carrier gas contacts said liquid flowing within said liquid directing means for a period of time sufficient to extract said volatile components within said flowing liquid forming a sample gas, said sample gas containing said extracted volatile components of said liquid and said carrier gas exiting said liquid directing means into said extraction container and exiting through said sample gas outlet port of said extraction container into said sample gas inlet port of said sample gas analyzing means; and Step 5. continuously analyzing said volatile components in said sample gas with said analyzing means.

10. A method in accordance with claim 9 wherein said liquid is water.

11. A method in accordance with claim 9 wherein said carrier gas is helium.

12. A method in accordance with claim 9 wherein said carrier gas supply means is a pressurized gas cylinder of helium having a pressure regulator and a valved flow meter.

13. A method in accordance with claim 9 wherein said sample gas analyzing means is a mass spectrometer.

14. A method in accordance with claim 9 wherein said liquid directing means extension is a length of tubing attached to said liquid directing means.

15. A method in accordance with claim 9 wherein said liquid inlet port depth changing means is a winch with a cable attached at one end to said liquid inlet port and attached at the other end to said liquid inlet port depth changing means for lowering and raising said liquid inlet port in said liquid source.

* * * * *